United States Patent [19]

Severin

[11] 4,316,291
[45] Feb. 23, 1982

[54] INTRAOCULAR LENS STRUCTURE

[76] Inventor: Stanford L. Severin, 1313 Solano Ave., Albany, Calif. 94706

[21] Appl. No.: 35,445

[22] Filed: May 3, 1979

[51] Int. Cl.³ .............................................. A61F 1/16
[52] U.S. Cl. ...................................................... 3/13
[58] Field of Search ............................................. 3/13

[56] References Cited

U.S. PATENT DOCUMENTS

| | | | |
|---|---|---|---|
| 3,866,249 | 2/1975 | Flom | 3/13 |
| 3,906,551 | 9/1975 | Otter | 3/13 |
| 3,925,825 | 12/1975 | Richards et al. | 3/13 |
| 3,971,073 | 7/1976 | Richards et al. | 3/13 |
| 3,994,027 | 11/1976 | Jensen et al. | 3/13 |
| 3,996,626 | 12/1976 | Richards et al. | 3/13 |
| 4,073,015 | 2/1978 | Peyman et al. | 3/13 |
| 4,079,470 | 3/1978 | Deeg et al. | 3/13 |
| 4,124,905 | 11/1978 | Clark | 3/13 |
| 4,136,406 | 1/1979 | Norris | 3/13 |
| 4,192,022 | 3/1980 | LaHaye | 3/13 |

OTHER PUBLICATIONS

Reshmi et al., "Pachymetric Evaluation of Corneal Thickness After Cataract Extraction and Intraocular Lens Implant"; *Amer. Intra-Ocular Implant Society Journal*; vol. 2, No. 1, pp. 17-21, Oct. 1976.

*Primary Examiner*—Clifford D. Crowder
*Attorney, Agent, or Firm*—John J. Leavitt

[57] ABSTRACT

Presented in several different aspects of the invention is a posterior chamber artificial lens structure adapted for implantation in the human eye. The lens structure includes an assembly comprised of a centrally disposed lens having an optically transparent portion through which light may be transmitted. The centrally disposed optically transparent lens portion is integral with an annular peripheral mounting portion the inner periphery of which is defined by the anchored ends of a plurality of separate support loops spaced circumferentially about the optically transparent lens portion. The outer periphery of the annular peripheral mounting portion is defined by an equatorial surface or edge disposed between the anterior and posterior surfaces of the lens. The separate lens support structures are preferably at least five in number and spaced circumferentially about the lens so that there is a substantially even distribution of separate support forces tending to retain the lens assembly properly positioned and supported on and by the iris in a zone surrounding the pupillary opening.

17 Claims, 14 Drawing Figures

INTRAOCULAR LENS STRUCTURE

BACKGROUND OF THE INVENTION

1. Field of the Invention

This invention relates to artificial lens structures for implantation in the human eye, and particularly to an artificial lens for intraocular implantation in the posterior chamber of the eye.

2. Description of the Prior Art

Prior art relating to this invention is believed to be found in Class 3, sub-class 13; Class 128, sub-class 76.5; and Class 351, sub-classes 40 and 160. A search through these classes and sub-classes has revealed the existence of the following nine U.S. Pat. Nos.: 3,458,870; 3,673,616; 3,711,870; 3,866,249; 3,906,551; 3,913,148; 3,925,825; 3,971,073 and 4,079,470.

It is noted that of these nine patents, there are only three that relate to lens structures adapted for implantation in the posterior chamber of the eye. Those three are U.S. Pat. Nos. 3,711,870; 3,866,249 and 3,913,148. Referring specifically to U.S. Pat. No. 3,711,870 this patent teaches the implantation of an artificial lens in the posterior chamber of the eye but does so by providing the lens with a resilient peripheral flange that is then sutured to the ciliary muscle to position the lens radially and axially in the eye. U.S. Pat. No. 3,866,249 also relates to a posterior chamber artificial intraocular lens structure, and also provides a peripheral flange surrounding the optical zone of the lens, with the peripheral flange being provided in turn with a plurality of prongs projecting from the lens structure that are adapted to be pushed through the stroma tissue of the iris which has the unique property of not healing when damaged by a tear or a puncture. U.S. Pat. No. 3,913,148 presents the concept of implantation of intraocular lens structure in the posterior chamber of the eye and provides a plurality of clips mounted to the central portion of the lens and extending outwardly from the face and toward the outer periphery. The clips are movable from an iris-receiving position to an iris-engaging position. In one embodiment disclosed by this patent the clips are resilient and their inherent resilience effects movement of the clips to bind the iris to the anterior surface of the lens structure, while in another embodiment, the clips are malleable and are physically moved into engaging position with the face of the iris tissue in the anterior chamber of the eye after insertion of the lens.

All of the remaining patents noted above, with the exception of the three discussed in detail, relate to intraocular lens structures that are specifically designed to be received in the anterior chamber of the eye rather than in the posterior chamber of the eye. Referring specifically to this latter group of patents, it is noted that U.S. Pat. No. 3,458,870 relates to an artificial corneal implant including a lens structure. The thrust of this patent is to the correction of corneal opacification by the insertion between surgically established anterior and posterior corneal layers of an artificial corneal implant one portion of which includes a lens structure. The patent does not teach the concept of insertion of a primary lens structure in the posterior chamber of the eye to replace the natural lens normally found in that position.

U.S. Pat. No. 2,673,616 is believed to be known in the art as the Binkhorst-Federov ocular lens, Mr. Binkhorst having written a paper for the British Journal of Opthomology, Volume 51 (1967), Pages 767-77. The lens structure taught by this patent is designed as an anterior chamber lens structure and includes a pair of oppositely disposed loops anchored to the backside of the lens at points spaced inwardly from the outer periphery of the lens, the rounded loops extending radially outwardly beyond the periphery of the lens. Additionally, the lens incorporates radially extending rods the inner ends of which are secured to the outer periphery of the lens so that the rods lie in a substantially median plane of the lens. When implanted, the two oppositely extending loops lie behind the iris in the posterior chamber of the eye while the three rods are positioned forwardly of the iris in the anterior chamber of the eye. One of the disadvantages of this lens is that the lens must be held in place by constriction of the pupil, thus requiring that the patient take miotic eye drops daily to maintain the lens in position. Obviously, should the pupils dialate for any reason, the lens can subluxate and require reinsertion.

U.S. Pat. No. 3,906,551 relates to an intraocular lens system including a lens body having a pair of oppositely projecting support loops extending radially beyond the periphery of the lens structure. Additionally, the lens body is provided with a haptic rim extending radially from its outer periphery and with a pair of apertures symetrically placed with respect to the loops and overlying the junction of the haptic rim and the outer periphery of the lens. The apertures are stated to be for the purpose of permitting the lens structure to be sutured to the iris.

U.S. Pat. No. 3,925,825 also relates to a lens structure for implantation in the anterior chamber of the eye rather than in the posterior chamber thereof. Briefly, the structure includes an optical lens member mechanically surrounded and enclosed by a support structure including a "wire" rim mounted on the periphery of the lens structure.

U.S. Pat. No. 3,971,073 teaches the concept of an intraocular lens structure adapted for implantation in the anterior chamber of the eye rather than posteriorly to the iris. The structure includes supporting loops extending radially from the lens structure, all of which project from the flat or planar side of the lens, the loops being axially offset from one another on the posterior side of the lens so as to provide a space therebetween for receiving the iris.

U.S. Pat. No. 4,079,470 relates to an anterior chamber lens incorporating a support structure sim ar to the support structure taught by U.S. Pat. No. 3,673,616 discussed above, but teaching the concept of incorporating a lens formed of a low density material or synthetic crystals such as corundum, sapphire, zircon, ruby, strontium titanate, diamond, anatase and rutile.

From the foregoing it will be clear that in this particular art even minute mechanical modifications in the construction of lens structures, whether they be for anterior or posterior implantation make a considerable and sometimes crucial difference as to the effectiveness of the lens. One of the problems appears to be the desirability of placing the artificial lens in as close to the position of the original natural lens as possible, which of course eliminates consideration of artificial lenses positioned in the anterior chamber of the eye. Another problem is preventing irritation of the inner surface of the cornea by impingement thereon of structure that might be used to fasten the artificial lens to the iris tissue.

Accordingly, it is one of the primary objects of this invention to provide an artificial intraocular lens structure that avoids these problems.

A problem that is particularly important with respect to both anterior chamber and posterior chamber lenses is the risk of damage that might result from the dislocation or subluxation of the lens structure at some time after implantation. Such dislocation may occur from violent body contact, from a blow to the eye, or from inordinate pressure exerted on the eye. In the case of a posterior chamber lens such as the one forming the subject matter of this invention, the problem is minimized by the construction of the lens forming the subject matter of this invention.

The invention possesses other objects and features of advantage, some of which, with the foregoing, will be apparent from the following description and the drawings. It is to be understood however that the invention is not limited to the embodiments illustrated and described since the invention may be embodied in various forms within the scope of the appended claims.

SUMMARY OF THE INVENTION

In terms of broad inclusion, the intraocular artificial lens of this invention has been designed specifically for posterior implantation in a human eye and in one of its aspects contemplates an optically clear lens member adapted to be mounted in the posterior chamber of the eye behind the pupillary opening of the iris in the position that was originally occupied by the natural lens of the eye. The optical portion of the lens is integral with a peripheral portion fabricated from the same material and having an outer peripheral portion of sufficient diameter to overlap the iris tissue under normal circumstances. To support the optical portion of the artificial intraocular lens structure in the posterior chamber of the eye, the lens is provided in one embodiment with a pair of diametrically opposed and radially extending generally U-shaped loop members the ends of the legs of which are embedded in the peripheral portion of the lens. Additionally, a plurality of additional loops, preferably three in number and also generally U-shaped in their configuration are mounted on the anterior side of the lens, the leg portions being embedded in the lens structure and projecting therefrom in an axial direction and then being turned outwardly so that they extend radially away from the central axis of the lens. The anterior and posterior loops are positioned in relation to one another to capture the peripheral edge of the iris between the loops in such a manner that the optical portion of the lens structure is mechanically supported in the posterior chamber of the eye in a position symmetrical with respect to the anterior-posterior axis of the eyeball with which the pupilary opening is also normally symmetrical.

In one of the embodiments illustrated herein one of the posterior loops and one of the anterior loops are positioned opposite each other in an axial direction while the remaining anterior loops are equally spaced about the lens portion of the structure. In another embodiment the anterior loops are equally spaced about the periphery of the lens structure but are off-set from the posterior loops. In a third embodiment two of the anterior loops are positioned 90° apart around the circumference of the optical lens portion while the remaining anterior loop is positioned 135° from the other two. As will hereinafter be seen, the positioning of these support loops is calculated to support the intraocular artificial lens in the posterior chamber of the eye in a position concentric to the pupilary opening of the iris and to do so without injuring or damaging the iris tissue in any way. In a fourth embodiment, the anterior loop positioned opposite the posterior loop is omitted, and in its place is substituted a stave which first passes over the inner peripheral portion of the iris, and is then "threaded" through the stroma tissue of the iris and locked behind the outer extremity of the posterior loop.

DESCRIPTION OF THE PREFERRED EMBODIMENT

Figure 1:
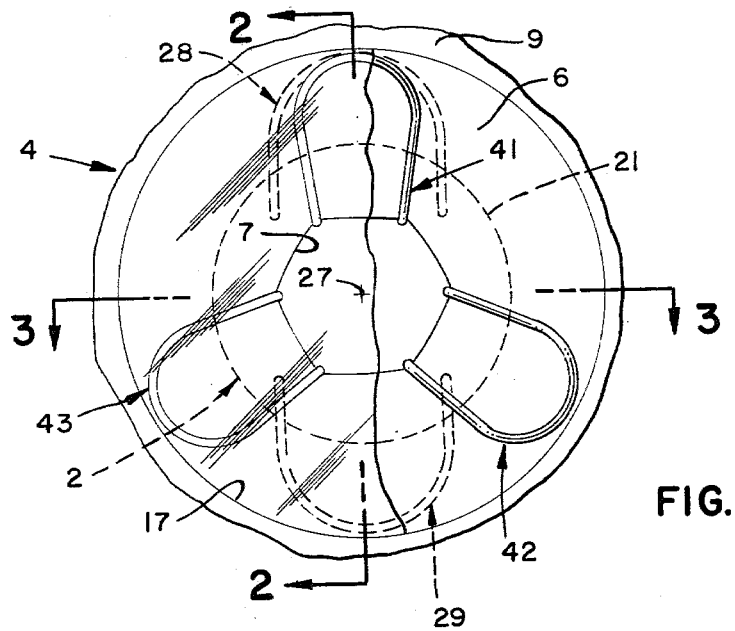
FIG. 1 is a fragmentary front elevational view of an eyeball with the artificial lens in place and showing a portion of the cornea cut away to expose a portion of the anterior surface of the iris and the lens.
Figure 2:
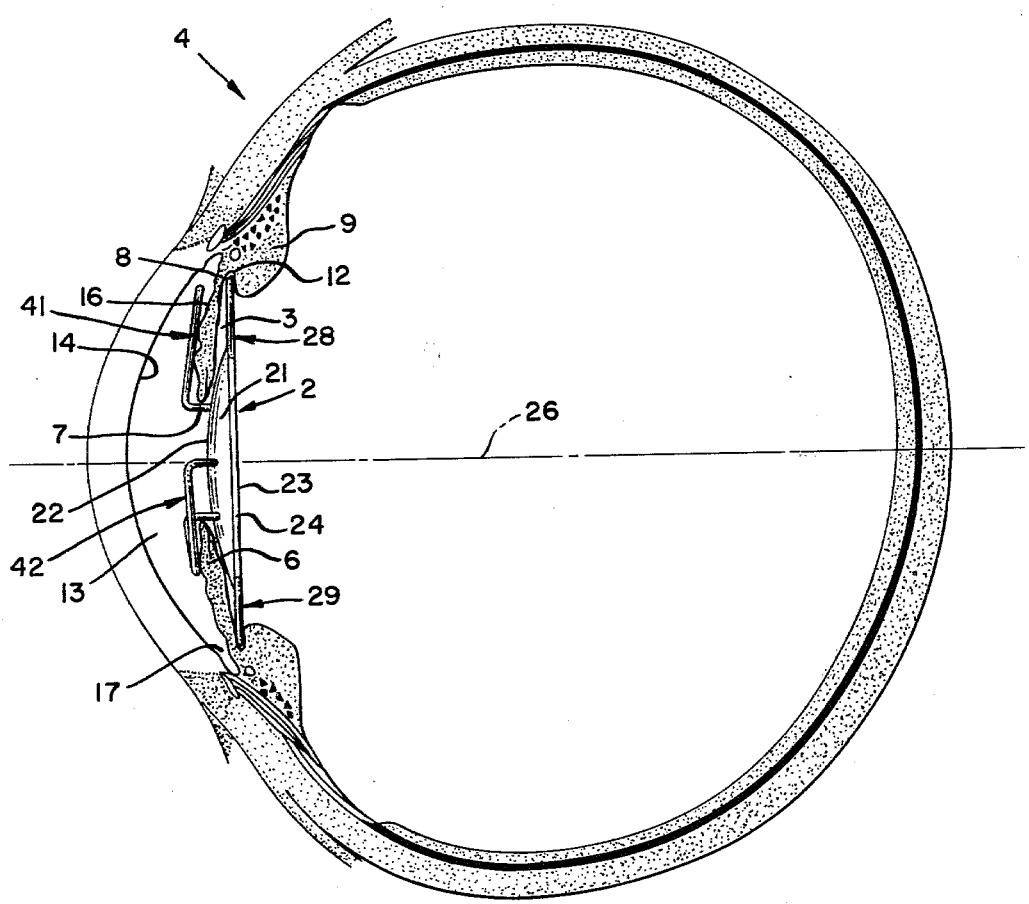
FIG. 2 is a vertical sectional view through the anterior-posterior axis of the eyeball showing one embodiment of the lens positioned in the posterior chamber of the eye.
Figure 3:
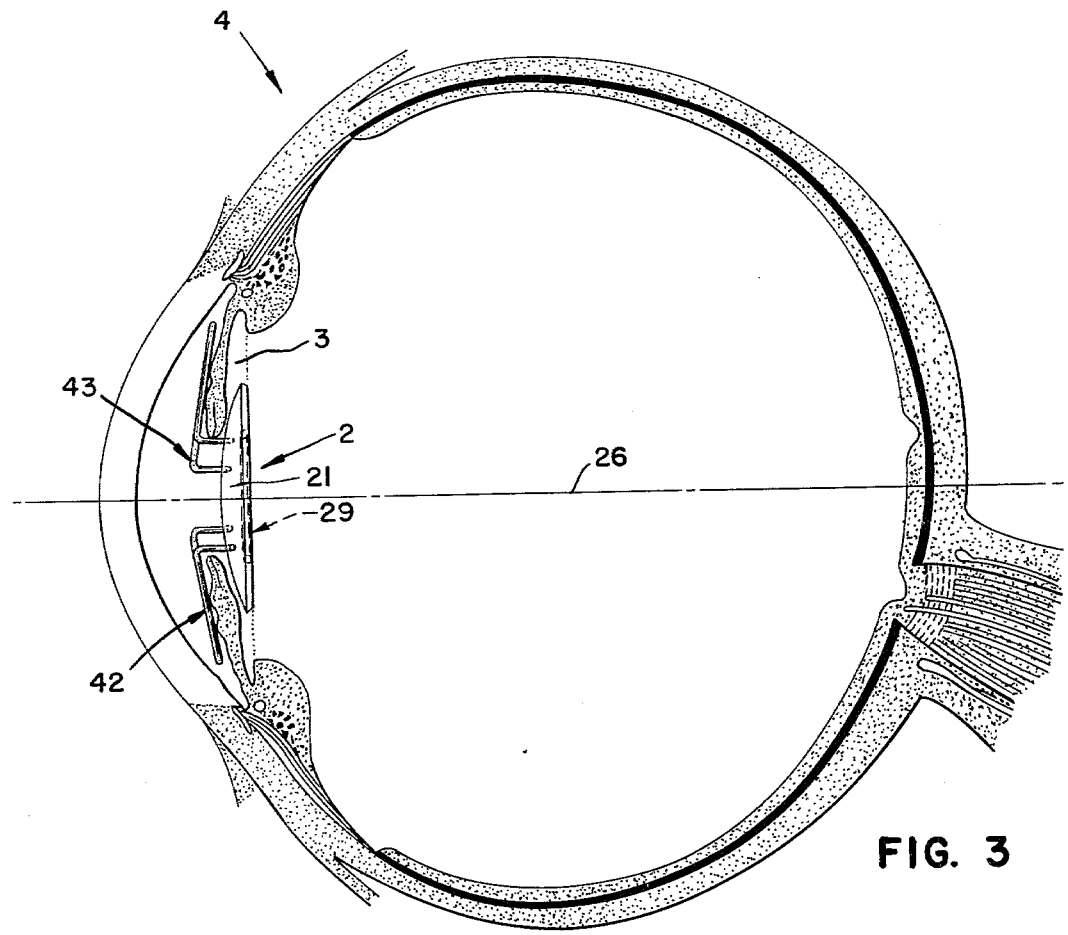
FIG. 3 is a horizontal sectional view through the anterior-posterior axis of the eyeball showing the lens positioned in the posterior chamber of the eye.

In terms of greater detail, the intraocular artificial lens structure of the invention as illustrated in FIGS. 1 through 5, inclusive, is designated generally by the numeral 2, and is supported in the posterior chamber 3 of the eyeball 4 as depicted in FIGS. 2 and 3. To develop an understanding of the extremely close spaces and distances that are involved in the optical system of the human eye, it should be noted that the anterior chamber of the eye is bounded in front by the cornea and a small portion of tissue identified as sclera; that viewed from in front, the cornea is eliptical in configuration, being approximately 12 millimeters in the horizontal direction and 11 millimeters in a vertical direction.

The cornea and sclera are structurally continuous and it is noted that only a very small amount of the sclera enters into the formation of the anterior chamber, these dimensions being in the order of approximately 2 millimeters above, 1.5 millimeters below and approximately 1 millimeter at the sides. The posterior wall of the anterior chamber is formed by the anterior surface of the iris, a part of the ciliary body and that portion of the lens which projects through the pupil. At the periphery of the anterior chamber there is formed a so-called "angle", this space opening inwardly toward the anterior-posterior axis of the eyeball where, measured between the anterior pole of the lens and the posterior pole of the cornea, the axial dimension of the space is approximately 3 millimeters.

The posterior chamber is somewhat triangular in cross section, the apex of the triangle being where the edge of the iris rests on the lens. In the normal eye provided with its natural lens, the base of the triangle in cross section is formed by the ciliary process which forms a continuation of the outer periphery of the iris, while the posterior wall of the posterior chamber is formed by the lens itself and the suspensory ligaments that support the lens in position. The anterior wall of this triangle is formed by the iris. Again, to illustrate the closeness of tolerances within the eye it should be noted that in the normal or natural eye the diameter of the lens is approximately 9 to 10 millimeters, its thickness from 4 to 5 millimeters measured between the anterior and posterior poles thereof, although this dimension varies to accomodate near vision and far vision in the normal eye.

It will thus be understood that an intraocular artificial lens adapted to be inserted into the posterior chamber of the eye must be formed in such a way that it may be suspended in essentially the same position that the natural lens was suspended, that it possess essentially the same relationship to associated eye elements such as the iris and the cornea as the natural lens, and that it be suspended in this position with security so that once implanted no further difficulty will be occasioned by dislocation of the artificial lens, and no irritation or at least minimal irritation be caused to the surrounding eye tissue.

Especially important is that the means selected for suspension of the artificial lens in the posterior chamber of the eye be of such type that the artificial lens is suspeneded in its proper position without danger that such suspensory means will come in contact with the inner surface of the cornea and thus damage that member. It is noted that in the natural lens, which as stated above, has a diameter of from 9 to 10 millimeters, it is only the central ⅓ of the lens that is effective to transmit light to the retina. That being the case, and since the weight of an artificial lens is an important factor in its fixation, I have determined that an artificial lens having a diameter of approximately 4.8 millimeters is substantially ideal because it encompasses a diameter sufficient to give effective transmission of light, say from 2.8 millimeters to 3 millimeters, while reducing the overall diameter and thereby reducing the overall weight.

Referring to FIGS. 1–3, it will there be seen that the artificial lens assembly 2 of the invention is positioned in the posterior chamber 3, the anterior wall of which is defined by the iris 6 the inner periphery 7 of which defines the pupil through which light is transmitted into the interior of the eye. The outer peripheral portion 8 of the iris forms a continuation of the ciliary body 9 and in the posterior chamber 3 the outer periphery of the iris and the ciliary body 9 form an annular recess 12 as shown. In the anterior chamber 13, the maximum depth of which it will be recalled is only approximately 3 millimeters, the inner posterior surface 14 of the cornea cooperates with the anterior surface 16 of the iris to form the "angle" 17 adjacent the outer peripheries of the iris and cornea as previously discussed.

The intraocular artificial lens assembly 2 inserted and securely mounted within this environment includes an optical portion 21 comprising the lens proper and provided with the convex anterior surface 22 and a posterior surface 23 which around their outer peripheries come into close juxaposed proximity and are integrally joined by an annular conical edge surface 24 forming the equator of the lens. An appreciation for the dimensional criticality of the structure can be secured when it is noted that the projected width of the conical surface 24 or "equator" about the outer periphery of the optical member or lens 21 is in the order of approximately 0.10 millimeters which is equivalent to approximately 0.004". It should of course be understood that while the optical member or lens 21 illustrated possesses a planar-convex configuration, the optical configuration of the lens member is dictated by the requirements of the particular patient and in some instances will have a greater depth than illustrated and in some instances will have a different configuration, for instance a convex-convex configuration.

To adequately support the optical or lens member 21 in the optimum position with respect to the anterior-posterior axis 26 of the eyeball, the intraocular artificial lens assembly 2 includes a plurality of mounting means securely attached to the lens member 21 and extending radially outwardly therefrom so as to encompass a portion of the iris in a manner so that the optical axis 27 (FIGS. 1, 4 and 5) will lie coincident with the anterior-posterior axis 26 of the eyeball to thus retain the lens member 21 symmetrical with respect to the pupilary opening of the iris defined by the inner periphery 7 thereof.

Figure 4:
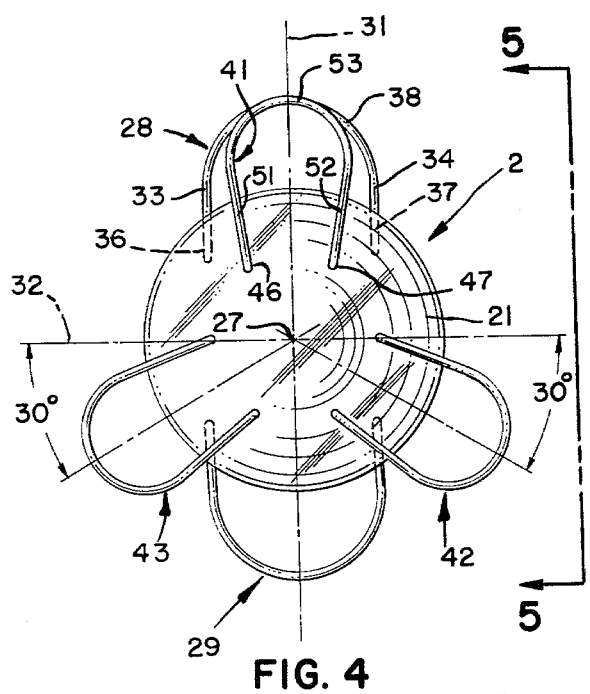
FIG. 4 is a front elevational view of the lens structure apart from the eye.

Referring to the embodiment of the intraocular artificial lens assembly illustrated in FIGS. 1 through 5, it will be seen that the mounting means comprises in this embodiment a pair of posterior support loops designated generally by the numerals 28 and 29, and lying in a common plane parallel to the posterior surface 23 of the lens 21 and generally bisecting the equatorial surface 24 surrounding the outer periphery of the lens 21. The posterior mounting or support loops 28 and 29 are positioned symmetrically with respect to a vertical plane 31 including the optical axis 27, and are also symmetrically positioned with respect to a horizontal plane 32 which also includes the optical axis 27, as seen in FIGS. 1 and 4.

Each of the posterior support loops 28 and 29 is generally U-shaped in its configuration, having leg portions 33 and 34 extending generally parallel to the vertical plane 31 and perpendicular to the horizontal plane 32 and having terminal end portions 36 and 37, respectively, extending into complimentarily extending and appropriately sized bores in the peripheral portion of the lens adapted to receive said terminal end portions. I have found that for maximum efficiency and to spread the pressure points of the posterior loops 28 and 29 against the posterior surface of the iris and to eliminate or minimize the possibility of irritation of the iris or ciliary body tissue, the support loop legs 33 and 34 are preferably spaced approximately 3 millimeters apart, i.e., 1.5 millimeters on opposite sides of the vertical plane 31, and extend radially outwardly to merge with a smoothly curved portion 38 the outer peripheral surface 39 of which is coincident with a circular arc having an approximately 8 millimeter diameter with its center coincident with the optical center of the lens. Stated another way, the outer peripheral surface 39 of each of the posterior supporting loops 28 and 29 lies spaced from the horizontal plane 32 approximately 4 millimeters.

It is preferred that the posterior supporting loops 28 and 29 be fabricated from a synthetic resinous material or "plastic" that is inert with respect to the various compounds found in the eye, particularly the aqueous humor, and that the lens 21 be fabricated from either the same material as the posterior supporting loops or such different material that is both optically suitable for the purpose intended and which is also inert with respect to the aqueous humor and other compounds found in the posterior chamber of the eye. It has been found that suitable support is derived from the posterior supporting loops 28 and 29 when the diameter of the material from which they are fabricated is approximately 0.20 millimeters which translates into approximately 0.008".

In addition to the posterior support loops 28 and 29, the support means for the artificial lens assembly also includes a plurality of anterior loops designated generally by the numerals 41, 42, and 43. The anterior support loops 41-43 are generally horseshoe-shaped when viewed anteriorly as in FIGS. 1 and 4, and in the embodiment of the invention illustrated in these FIGS. 1-5, it will be seen that the anterior support loops are positioned at equal circumferential intervals of 120° about the optical axis 27, the loops extending radially outwardly so that they lie circumscribed by a circle having a radius of approximately 4 millimeters, as are the posterior support loops 28 and 29. In the interest of brevity in this description, the loop 41 will be described in detail and the description of this loop will apply to the other two loops with the exception of the position thereof in relation to the optical member 21.

Figure 5:
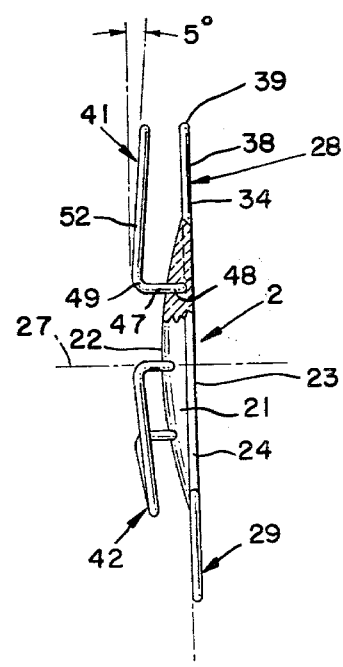
FIG. 5 is a side elevational view partly in section taken in the direction indicated by the arrows 5—5 in FIG. 4.

Referring to FIGS. 4 and 5, it will be seen that the anterior support loop 41 is anchored to the lens member 21 so that it projects axially from the anterior surface 22 thereof. To accomplish such axial projection of the anterior legs, each loop is provided with a pair of anchor legs 46 and 47, each having portions 48 embedded and retained in the body of the lens member 21 and projecting axially therefrom parallel to the optical axis of the lens member 21 and parallel also to the vertical and horizontal planes 31 and 32. These anchor legs 46 and 47 project a predetermined distance from the convex surface of the lens member 21 at their point of emergence therefrom of approximately 0.7 millimeter and then turn radially outwardly in a bend portion 49 that merges smoothly into radially outwardly projecting leg portions 51 and 52 which are angularly disposed with respect to the vertical plane 31 and which merge smoothly into a circular outer peripheral portion 53 having a diameter of approximately 2.16 millimeters. It is noted that the diameter of the curved or semi-circular portion 53 of the anterior loop is greater in a transverse dimension than the spacing between the leg portions 46 and 47, thus contributing the "horseshoe" configuration to the anterior loop.

It is important to note that in their radial extension from the bend 49 and the union of legs 51 and 52 with anchor portions 46 and 47, the legs 51 and 52 and loop portion 53 are not parallel to the posterior surface 23 of lens 21 and not parallel to the plane containing the posterior support loops 28 and 29. Rather, each of the anterior loops 41, 42 and 43 is inclined rearwardly or posteriorly so that in converges toward the plane containing the posterior loops 28 and 29, such convergence being effected so that the anterior support loops are inclined to such plane containing the posterior loops at an angle of approximately 5°. This is important because, as viewed in FIGS. 2 and 3, the iris projects anteriorly from an outer peripheral portion 8 at approximately the same angle, thus resulting that when in proper position, the anterior loops 41-43 lie substantially parallel to the anterior surface of the iris.

Additionally, since it is important that the artificial lens be supported uniformly about its optical axis 27, it will be noted that the support leg portions 46 and 47 of the anterior support loop are positioned at equal intervals about the optical axis 27 on a base circle having a radius of approximately 1.4 millimeters or a diameter of 2.8 millimeters, thus placing the support legs 46 and 47 of each of the anterior loops at the outer fringe of the effective optical area of the lens 21. As with the posterior support loops 28 and 29, the anterior support loops are preferably fabricated from a cylindrical synthetic resinous material having a diameter of approximately 0.20 millimeters or 0.008 inches. Another relationship that is important is that the depth to which the anchor portions 36 and 37 of the posterior support loops 28 and 29 project into the peripheral portion of the lens 21 places the extreme inner ends of these support portions outboard from the anchor legs 46 and 47 as clearly shown in the drawing.

As seen clearly in FIG. 4, the anterior loop 41 is positioned on the lens 21 so that it is opposed to the posterior loop 28 and with the posterior loop 38 bisected by the vertical plane 31. The other two loops 42 and 43 are circumferentially spaced from the anterior loop 41 by approximately 120° so that a plane including the optical axis 27 and bisecting these anterior loops 42 and 43 will be angularly disposed with respect to the horizontal plane 32 by approximately 30°.

It will thus be seen that when the intraocular artificial lens is implanted in the human eye, the exterior peripheries 39 of the posterior support loops 28 and 29 project snugly but not in any deliterious manner into the annular channel 12 formed between the outer periphery 8 of the iris and the ciliary body 9. It is possible that a slight space may exist between the posterior surface of the iris and the anterior surface of the posterior support loops 28 and 29 as shown in FIG. 2, however because of the relatively wide stance of the support legs 33 and 34 it will also be apparent that the soft accordian pleated portion of the iris may present itself posteriorly through the space between the support legs 33 and 34 of both loops, thus tending by such presentation to prevent rotation of the artificial lens about the optical axis 27.

Additionally, it is likely that the same presentation of iris tissue may occur with respect to the anterior loops 41-43, the soft accordian pleated tissue of the iris presenting itself through the opening between support legs 51 and 52 which, because of their inherent resilience and delicate construction, do not chafe or otherwise damage the iris. Because the peripheral portion of the iris thickens as it joins the ciliary body 9, at an intermediate point spaced from the outer peripheral portion of the iris the iris tissue has a thickness that is somewhat less than the base or outer peripheral portion. Accordingly, because of the desirability of preventing contact of the anterior support loops 41–43 with the endothelium of the cornea, the outer and smoothly curved circular portion 53 of each of the anterior support loops is designed to rest snugly in this thinned portion of the iris so as to place it as far as possible from the endothelium of the cornea. It is for this reason that each of the anterior loops is angularly disposed approximately 5° with respect to the plane of the posterior support loops 28 and 29.

Because fixation of the artificial lens in the eye is so important, I have found that placing the anchor portions 46 and 47 of each of the anterior support loops 41–43 equally spaced about a base circle having a diameter of approximately 2.8 millimeters results in the inner periphery 7 of the iris being placed under a slight amount of tension when the intraocular artificial lens is implanted. Referring to FIG. 1, it will there be seen that such slight amount of tension imposed on the inner periphery of the iris results in the configuration of the inner periphery of the iris or pupilary opening being transformed from a circular configuration to a substantially hexagonal configuration as illustrated.

It will thus be seen that the radial distance between the optical axis 27 of the lens structure and each of the axially extending support legs 46 and 47 is greater than the radial distance between the optical axis 27 and the relatively straight chordal portion of the pupilary opening. While it is not believed that iris tissue takes a "set" as do some other elements, it is obvious that retaining the inner periphery of the iris or pupilary opening in a hexagonal configuration as illustrated will help to prevent rotational dislocation of the artificial lens structure with respect to the optical axis 27, the horizontal plane 32 and the vertical plane 31, thus resulting in a very secure fixation of the artificial lens structure within the posterior chamber of the eye.

Figure 6:
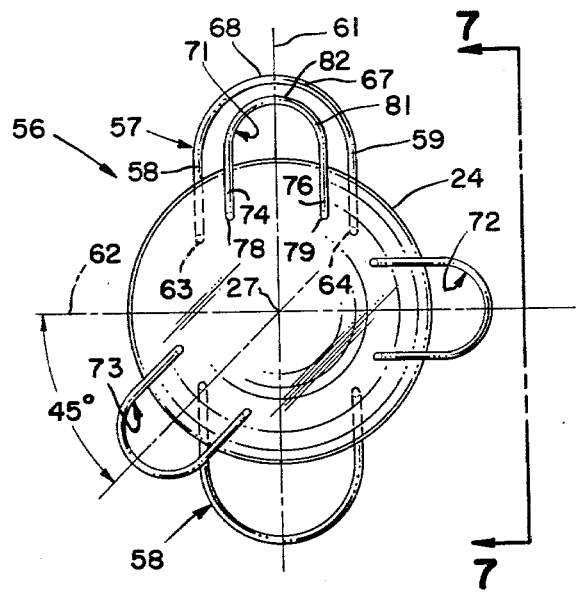
FIG. 6 is a front elevational view of another embodiment of the invention.
Figure 8:
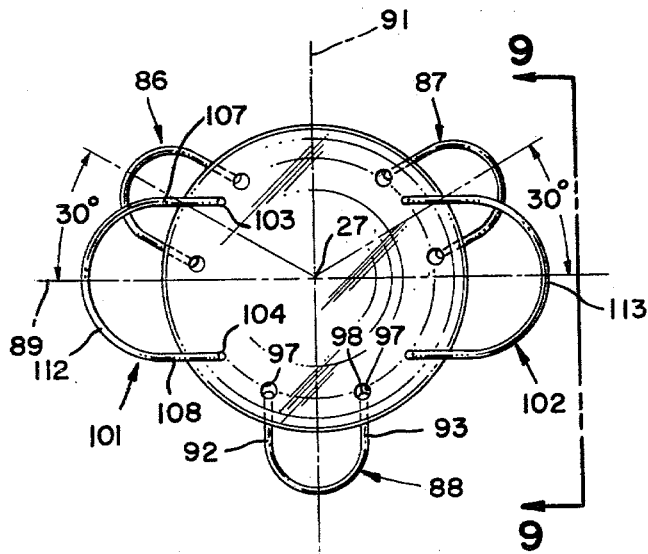
FIG. 8 is a front elevational view of a third embodiment of the invention.

It is believed that the use of five support loops is so effective in fixation of an intraocular artificial lens assembly in the posterior chamber of the eye that the embodiments illustrated in FIGS. 6 and 8 have been presented as alternatives to the embodiment illustrated in FIGS. 1 and 4. With some patients, depending upon the condition of the iris, there may be a tendency for the iris tissue to bunch up between circumferentially spaced supports and it is therefore desirable to have an alternative structure available that may be utilized when the condition of the patient's iris dictates such alternative structure or arrangement. In other instances, it may be found that the iris tissue is so sensitive as to be irritated by the pressure exerted by two opposed support loops such as the support loops 41 and 28 in FIG. 4. Under these conditions, it is adviseable to have available an alternative structure as illustrated in FIG. 8 in which the support loops are circumferentially spaced from one another as hereinafter described.

In the embodiment of the invention illustrated in FIG. 6, it will be noted that the lens 21 has the same configuration as the lens in the embodiment illustrated in FIGS. 1–5, and is therefore designated by the same numeral. In this embodiment, the intraocular lens assembly as a whole is designated generally by the numeral 56 and includes a pair of radially extending posterior support loops designated generally by the numerals 57 and 58, the loops being identical and in the interest of brevity the description of one applies to the other.

Figure 7:
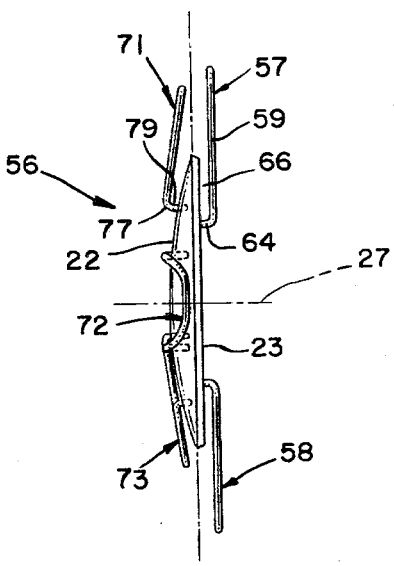
FIG. 7 is a side elevational view of the embodiment shown in FIG. 6.

Thus, the posterior loop 57 is provided with a pair of radially extending support legs 58 and 59 parallel to one another and parallel to the vertical plane 61 and perpendicular to the horizontal plane 62, both of which planes include the optical axis 27. At their ends, the support legs 58 and 59 merge smoothly with axially extending support portions 63 and 64 (FIGS. 6 and 7) anchored in the lens body and projecting axially from the posterior surface 23 of the lens 21 so as to provide a space 66 between such posterior surface 23 and the radially extending leg portions 58 and 59 of the U-shaped posterior support loop 57. The support legs 58 and 59, as seen in FIG. 6, project radially and merge smoothly with a circular support portion 67 the other peripheral surface 68 of which lies approximately four (4) mm from the optical axis 27, the loop lying symmetrical with respect to the vertical plane 61 and the support leg portions 63 and 64 being embedded in the body of the lens 21 at points equidistant about a base circle (not shown) having a radius of approximately 2.1 mm. It will thus be seen that the overall length of the posterior support loops 57 and 58 are somewhat longer than the corresponding posterior support loops 28 and 29 in FIG. 4, resulting in the posterior loops 57 and 58 having somewhat greater flexibility or "softness" by virtue of a longer lever arm, and therefore useful in instances where such "softness" is required by the condition of the iris on which it is to be supported.

This embodiment of the invention is also provided with three anterior loops designated generally by the numerals 71, 72 and 73, these anterior loops being fabricated from the same material as the anterior loops in FIGS. 1–5, and differentiating therefrom in the circumferential placement of the anterior loops and in the spacing of the attachment legs to the anterior surface 22 of the lens. Thus, referring to the anterior loop 71, which is identical to the loops 72 and 73, each loop is provided with radially extending support legs 74 and 76 parallel with vertical plane 61 and angularly disposed with respect to horizontal plane 62. Each of the legs 74 and 76 merge smoothly with a bend 77 which in turn merges smoothly with and is integral with axially extending leg portions 78 and 79 that project into and lie embedded in the body of the lens 21. It should be noted that the positional relationship of these legs 78 and 79 is such that they lie on the same base circle on which the support legs 63 and 64 of the posterior support loops lie. Stated another way, these support leg portions 63 and 64 are spaced from the optical axis 27 of the lens the same distance as support leg portions 78 and 79.

Each of the support legs portions 74 and 76 merges smoothly with a curved support portion 81 which, with respect to the anterior support loop 71, lies opposite the posterior support loop 57 as shown in FIG. 6. It should be noted also that the outer peripheral surface 82 lies intermediate the outer peripheral surface 68 of the posterior support loop and the outer periphery 24 of the lens. This results in a somewhat shorter anterior support loop than the support loop utilized in the embodiment illustrated in FIGS. 1–5, and therefore increases the "stiffness" of the anterior support loops in this embodiment. As with the anterior support loops of the embodiment illustrated in FIGS. 1–5, the anterior support loops of this embodiment are also angularly disposed approximately 5° with respect to a plane including the peripheral edge of the lens 21.

Of the remaining anterior support loops, referring to FIG. 6, the anterior support loop 72 is shown positioned 90° clockwise when viewed anteriorly with respect to the support loop 71, while the anterior support loop 73 is positioned 135° counterclockwise from the anterior support loop 71, or stated another way, the support loop 73 is positioned symmetrical with respect to a plane 135° clockwise from plane 62, both planes including the optical axis 27 of the lens.

As with the embodiment of the artificial lens assembly illustrated in FIGS. 1–5, it is anticipated that this embodiment of the invention will be implanted by first inserting the posterior loop 58 behind the iris at the 6:00 o'clock position and carefully threading the inner periphery of the iris between the anterior loop 73 and the posterior loop 58. Thereafter, the upper or 12:00 o'clock periphery of the iris is carefully threaded between the posterior loop 57 and the opposed anterior loop 71 and any adjustment of position of the artificial lens assembly is accomplished by carefully grasping the root portions of the radially extending legs 74 and 76 of the anterior support loops and effecting whatever adjustment is required to place the optical axis 27 of the artificial lens assembly in coincidence with the anterior-posterior axis of the eyeball.

With this embodiment of the invention it will be noted that because the support leg portions 78 and 79 of the anterior support loops are spaced radially outwardly somewhat farther than the corresponding elements illustrated in FIGS. 1–5, the pupillary opening will be somewhat larger in diameter, with the result that, depending on the patient, there will be somewhat greater tension in the inner peripheral portion of the iris where it contacts the support leg portions 78 and 79 at six locations. Even so, there is sufficient peripheral distance between the support leg portions 78 and 79 and the outer periphery of the lens 21 to permit the iris to dilate normally without fear that the pupillary opening will be so great as to cause dislocation of the artificial lens assembly in an anterior or posterior direction.

Figure 9:
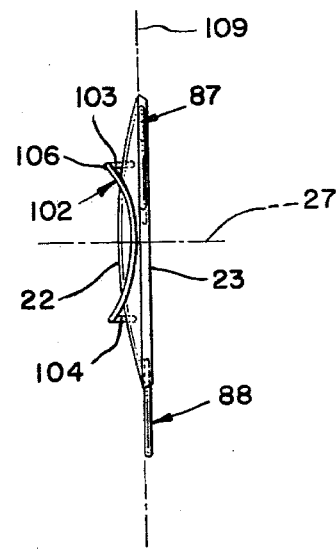
FIG. 9 is a side elevational view of the FIG. 8 embodiment.
Figure 10:
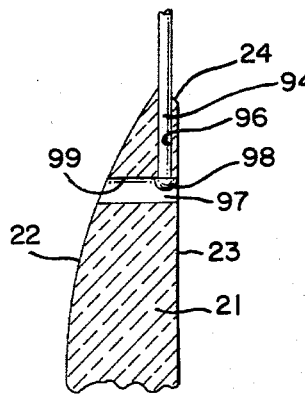
FIG. 10 is a fragmentary sectional view partly in elevation illustrating one technique for anchoring the legs of some of the lens support loops.
Figure 11:
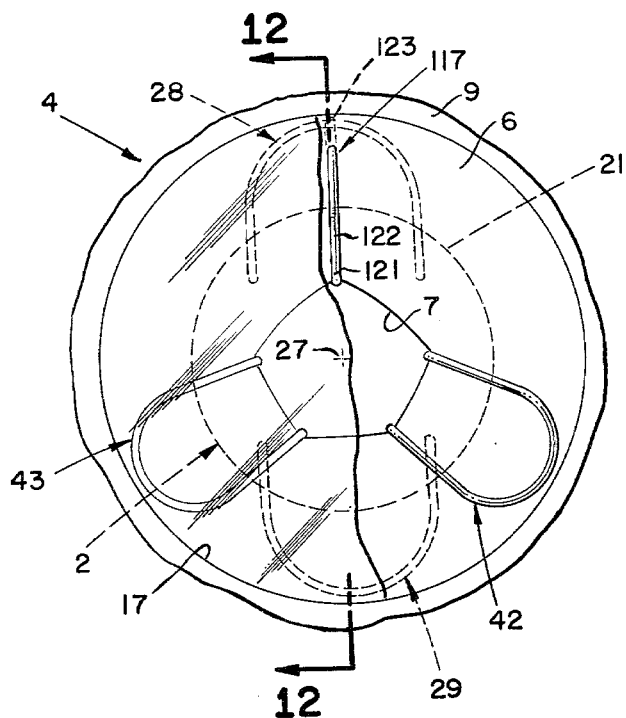
FIG. 11 is a fragmentary front elevational view similar to FIG. 1 of a fourth embodiment which substitutes a stave for the anterior loop positioned opposite the posterior loop, the stave having anterior and posterior portions.
Figure 12:
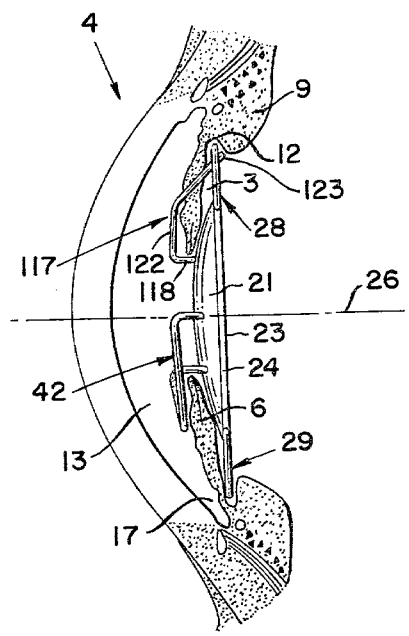
FIG. 12 is a fragmentary vertical sectional view of the embodiment of FIG. 10 illustrating the posterior portion of the stave captured behind the posterior loop after having been passed through the stroma tissue of the iris.

The embodiment of the invention illustrated in FIGS. 8–10 is similar in its purpose to the other two embodiments, and like those embodiments, utilizes five support loops for effecting fixation of the artificial lens assembly in the posterior chamber of the eye. In this embodiment, while five supporting loops are provided, it will be seen from reference to FIG. 8 that three posterior support loops designated generally by the numerals 86, 87 and 88 are provided, these three posterior loops being equally spaced around the periphery of the lens 21 at 120° intervals. It is sometimes desirable that lateral stability of the artificial lens assembly in the posterior chamber of the eye dominate vertical stability. For this reason, it will be noted that the posterior support loops 86 and 87 are spaced 30° circumferentially from a horizontal plane 89 which includes the optical axis 27 while the third posterior loop 88 is in the 6:00 o'clock position, extending downwardly, and bisected by a vertical plane 91 which also includes the optical axis 27 and with respect to which the posterior support loop 88 is symmetrical.

An additional feature of this embodiment is that all of the posterior support loops 86–88 are attached to and project from the inclined equatorial surface 24, of the lens body, each of the posterior loops being provided with radially extending legs 92 and 93 whose root portions 94 (FIG. 10) extend into an appropriate bore 96 extending radially into the body of the lens 21 through the equatorial surface 24 for a distance sufficient to intercept an axially extending bore 97 communicating between the posterior surface 23 of the lens and the anterior surface 22 thereof. Within the axial bores 97, the ends 98 of each of the inwardly extending support legs 92 and 93 is appropriately fused to the inner periphery 99 of the bore 97. In addition to functioning as a means to fuse the end of each leg portions 92 and 93 to the lens body, the bores 97 also function as drain passages to provide for the free flow of aqueous humor from the ciliary body to the front of the lens and to the anterior chamber.

As previously discussed, the posterior support loops 86–88 are fabricated from a synthetic resinous material that is essentially neutral when immersed in the aqueous humor found in the posterior chamber of the eye, and is formed from a filament having a circular cross-section and a diameter of approximately 0.20 mm or 0.008". Because the posterior loops 86–88 project from the circular periphery 24 of the lens 21, it will be noted that they thereby present a relatively short lever arm and possess somewhat more "stiffness" than the anterior and posterior loops of the embodiment illustrated in FIG. 6.

In this embodiment (FIG. 8) there are only two anterior loops provided and these are designated generally by the numerals 101 and 102. As seen in FIG. 8, the pair of anterior support loops 101 and 102 project in opposite directions and are symmetrical with respect to the horizontal plane 89 including the optical axis 27 of the lens. Thus, when the artificial lens assembly is implanted, the anterior loops 101 and 102 lie in the 9:00 o'clock and 3:00 o'clock positions, respectively, and overlie the iris in a manner to cooperate with the posterior loops to fix the assembly in the posterior chamber of the eye so that the optical axis 27 of the lens coincides with the anterior-posterior axis of the eyeball.

Each of the anterior loops 101 is provided with axially extending support leg portions 103 and 104 which lie embedded in the body of the lens and which emerge therefrom and project above the anterior surface of the lens approximately one-half a millimeter to merge smoothly with a bend 106 which in turn merges smoothly with radially outwardly extending support legs 107 and 108 which extend parallel to the horizontal plane 89 and angularly disposed with respect to the vertical plane 91 and converging toward a plane 109 within which the posterior loops 86–88 are contained. The support leg portions 107 and 108 merge smoothly with a circular support portion 112 the outer peripheral surface 113 of which determines the maximum transverse dimension of the assembly and measures approximately 8 mm. As illustrated in FIGS. 8 and 9, the support leg portions 103 and 104 are embedded and securely anchored in the lens 21 at equally spaced intervals about a base circle (not shown) disposed between the outer periphery 24 of the lens and the optically active central portion of the lens. Thus, when implanted, the pupillary opening of the iris is determined by the radial spacing of the support leg portions 103 and 104 on the pair of anterior support loops, while the remainder of the anterior peripheral portion of the lens spaced radially outwardly from these support leg portions impinges lightly against the posterior surface of the iris yet is of sufficient width as to permit the iris to dilate to a maximum pupillary opening without danger of dislocating the lens.

Figure 13:
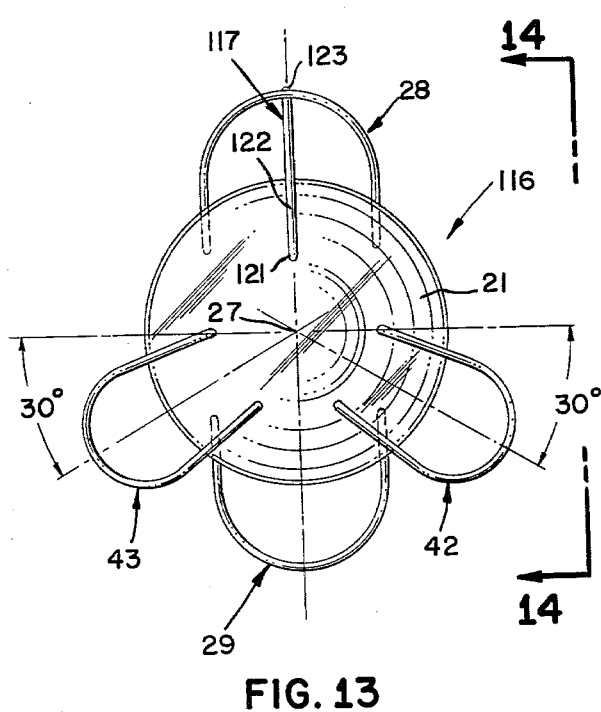
FIG. 13 is a front elevational view of the FIG. 10 embodiment apart from the eye.
Figure 14:
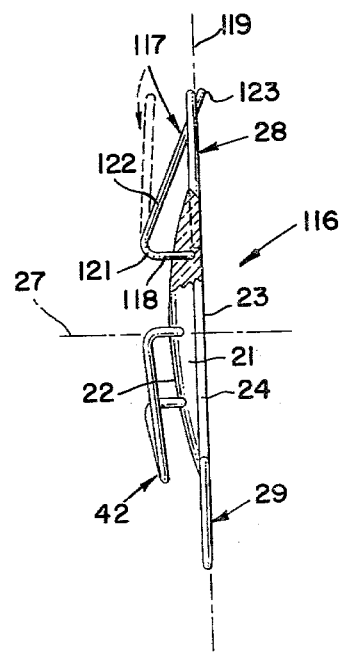
FIG. 14 is a side elevational view of the FIG. 10 embodiment apart from the eye and viewed in the direction of the arrows 13—13 in FIG. 12.

The embodiment illustrated in FIGS. 11–14 is similar in some respects to the embodiment of the invention illustrated in FIGS. 1 through 5, but differs in that the anterior loop at the 12 o'clock position as provided in FIG. 4 is eliminated from the embodiment illustrated in FIGS. 13 and 14. In lieu of the anterior loop 41, this embodiment of the invention is designated generally by the numeral 116 and, with the exception of the anterior loop 41, includes all of the elements of the embodiment illustrated in FIG. 4. Accordingly, in the interest of brevity, the same reference numbers have been applied to corresponding elements of the combination.

In lieu of the anterior loop 41, the embodiment of FIGS. 11–14 includes a stave designated generally by the numeral 117, provided with a mounting portion 118 the end of which is embedded and permanently secured to the lens body as shown with the mounting portion 118 extending from the anterior face of the lens generally perpendicular to the plane 119 including the posterior surface of the lens. The mounting portion 118 is integral with and merges smoothly with a bend 121 which in turn merges with a radially extending portion 122 which is inclined rearwardly or merges toward the plane 119. The stave is provided with an extreme end portion 123 that is locked or latched behind the posterior loop 28 as shown in FIG. 14.

It is preferred that when this lens structure is manufactured that the stave 117 be provided with a "set" so that its normal unbiased position is the latched or locked position illustrated in FIG. 14. During the surgical procedure to implant the lens assembly, the stave 117 is retracted into the position shown in broken lines. While held in this position in relation to the posterior loop 28, the thin peripheral edge portion of the iris at the 12 o'clock position is threaded between the posterior loop 28 and stave 117. Then, to effect locking of the stave 117 behind the posterior loop 28, the surgeon makes an extremely small incision through the stroma tissue surrounding the iris and carefully threads the stave 117 through the incision thus made, and causes the stave 117 to be locked behind the posterior loop 28.

It will thus be seen that this alternative construction of the intraocular artificial lens assembly not only provides lateral stability by preventing lateral displacement of the lens assembly, but it also prevents vertical displacement. In addition, the interengagement of the stave 117 through the iris tissue and its locking relationship with the posterior loop 28 prevents rotational dislocation of the lens assembly. It will thus be seen that this construction can be used in patients where the iris tissue is extremely fragile and thin and not sufficiently supportive of the lens assembly merely through the use of anterior and posterior loops as disclosed and illustrated in the previous three embodiments.

Having thus described the invention, what is claimed to be new and novel, and sought to be protected by Letters Patent of the United States is as follows:

I claim:

1. An intraocular artificial lens assembly for surgical implantation in the posterior chamber of a human eye the iris and pupillary opening of which are coaxially symmetrical about the anterior-posterior axis of the eye, comprising:
   (a) a lens member having a posterior surface including a posterior pole, an interior surface including an anterior pole, an equatorial surface disposed between said posterior and anterior surfaces, said posterior and anterior surfaces being substantially symmetrical with respect to an optical axis including said posterior and anterior poles, a generally centrally disposed optically active portion of predetermined minimum transverse dimension correlated to the pupillary opening, and an annular peripheral portion circumscribing said optically active portion;
   (b) at least five separate support means separately mounted on said lens member and projecting radially outwardly past said equatorial surface so as to leave substantial portions of said equatorial surface unobstructed;
   (c) at least four of said five separate support means comprising generally U-shaped support loops, each support loop including a pair of spaced legs merging smoothly at one end into an integral curved portion common to both legs of the pair of spaced legs, said integral curved portion lying radially outwardly spaced from said equatorial surface, said spaced legs at their opposite ends being fixed to said lens member in circumferentially spaced relationship;
   at least two of said separate support means being mounted on said lens member in a plane perpendicular to said optical axis and arranged to engage selected posterior surfaces of the iris and the remainder of said separate support means being mounted on the anterior surface of said lens member and converging toward said plane to engage selected anterior surfaces of the iris;
   said separate support means mounted on the anterior surface of said lens member each having at least one integral support portion embedded in said lens member and extending from the anterior surface in the direction parallel to said optical axis so that said anterior separate support means are spaced from the anterior surface of said lens member, whereby said lens member is adapted to be suspended on the iris with said annular peripheral portion of said lens member and said posterior support means engaging the posterior surface of the iris, with said anterior support means engaging the anterior surface of the iris, and with the integral support portions of said anterior support means adapted to engage the peripheral surface of the pupillary opening in the iris so that the optical axis of the lens member coincides with the anterior-posterior axis of the eye.

2. The combination according to claim 1, in which at least two of said four support loops are adapted to engage the anterior surface of the iris and three of said support means including at least two support loops are adapted to engage the posterior surface of the iris.

3. The combination according to claim 1, in which said at least two of said support loops project radially from said equatorial surface.

4. The combination according to claim 1, in which said separate support means are arranged in relation to a a vertical plane and a horizontal plane within both of which said optical axis is included, at least two of said support loops being symmetrically arranged in relation to at least one of said planes and being bisected thereby.

5. The combination according to claim 1, in which the ends of said legs of said U-shaped loops are anchored to said lens member at points radially outwardly spaced from said centrally disposed optically active portion of the lens member.

6. The combination according to claim 1, in which said five separate support means comprise five generally U-shaped support loops opening toward said optical axis.

7. The combination according to claim 1, in which two of said five separate support means constitute a pair of diametrically opposed support loops.

8. The combination according to claim 4, in which said two diametrically opposed support loops constitute posterior loops engageable with the posterior surface of the iris.

9. The combination according to claim 4, in which said two diametrically opposed support loops constitute anterior loops engageable with the anterior surface of the iris.

10. The combination according to claim 1, in which said at least two of said five separate support means constitute a pair of diametrically opposed support loops, one of said remainder of said five separate support means being cooperatively associated opposite one of said two diametrically opposed support loops.

11. The combination according to claim 10, wherein said remainder of said five separate support means are equally spaced circumferentially about said lens member.

12. The combination according to claim 11, wherein said one of said remainder of five separate support means is a stave adapted to lock behind said one of said two diametrically opposed support loops.

13. The combination according to claim 1, in which three of said five separate support means constitute U-shaped support loops anchored to the anterior surface of the lens member at circumferentially spaced points spaced radially inwardly from the equatorial surface of the lens member.

14. The combination according to claim 13, in which the remaining two separate support means constitute a pair of diametrically opposed support loops having spaced leg portions integral with said curved portions anchored to the lens member at said equatorial surface.

15. The combination according to claim 1, in which two of said five separate support means constitute a diametrically opposed pair of support loops including spaced leg portions the inner ends of which are anchored to said anterior surface of said lens member at points spaced radially inwardly from said equatorial surface, the remaining three separate support means constituting support loops equally spaced circumferentially about said lens member and including spaced leg portions the inner ends of which are anchored to said lens member at points spaced radially inwardly from said equatorial surface.

16. The combination according to claim 1, in which said at least two of said separate support means constitute a pair of diametrically opposed support loops including spaced leg portions anchored to said lens member at said equatorial surface, one of said remaining three separate support means constituting a stave anchored at one end on said anterior surface of said lens and including an axially extending mounting portion adapted to be engaged by the inner periphery of the iris and an integral radially outwardly extending portion the inner end portion of which adjacent said axially extending mounting portion is adapted to engage the anterior surface of the iris while the end portion of the stave remote from the axially extending mounting portion is adapted to engage the posterior surface of the iris and to lock behind an associated one of said pair of support loops, the remaining two separate support means constituting support loops circumferentially spaced from said stave and adapted to engage the anterior surface of the iris.

17. The combination according to claim 1, in which one of said five separate support means constitutes a stave anchored at one end of the anterior surface of the lens and projecting radially outwardly with a portion adapted to engage the anterior surface of the iris, a portion adapted to engage the posterior surface of the iris and an end portion adapted to interengage with one of the remaining four separate support means, two of which constitute posterior support loops and two of which constitute anterior anterior support loops.

* * * * *